United States Patent
Griffith et al.

(10) Patent No.: US 8,449,528 B2
(45) Date of Patent: May 28, 2013

(54) ENTERAL FEEDING EXTENSION SET CONNECTOR

(75) Inventors: Nathan C. Griffith, Roswell, GA (US); Donald J. McMichael, Roswell, GA (US); John A. Rotella, Roswell, GA (US); Scott M. Teixeira, Cumming, GA (US)

(73) Assignee: Kimberly-Clark Worldwide Inc., Neenah, WI (US)

( * ) Notice: Subject to any disclaimer, the term of this patent is extended or adjusted under 35 U.S.C. 154(b) by 201 days.

(21) Appl. No.: 12/977,677

(22) Filed: Dec. 23, 2010

(65) Prior Publication Data

US 2012/0029483 A1  Feb. 2, 2012

Related U.S. Application Data

(60) Provisional application No. 61/369,432, filed on Jul. 30, 2010.

(51) Int. Cl.
| | |
|---|---|
| *A61M 25/16* | (2006.01) |
| *A61M 25/18* | (2006.01) |
| *A61M 39/00* | (2006.01) |
| *A61M 39/02* | (2006.01) |
| *A61M 39/10* | (2006.01) |

(52) U.S. Cl.
USPC ........... 604/535; 604/533; 604/534; 604/538; 604/539

(58) Field of Classification Search
USPC .................. 604/533, 534, 535, 537, 538, 539
See application file for complete search history.

(56) References Cited

U.S. PATENT DOCUMENTS

| | | | |
|---|---|---|---|
| 5,836,924 | A | 11/1998 | Kelliher et al. |
| 6,458,106 | B1 | 10/2002 | Meier et al. |
| 6,736,797 | B1 | 5/2004 | Larsen et al. |
| 6,802,836 | B2 | 10/2004 | Bouphavichith et al. |
| 6,976,980 | B2 | 12/2005 | Brenner et al. |
| 6,979,322 | B2 | 12/2005 | Chu et al. |
| 2005/0107743 | A1 | 5/2005 | Fangrow, Jr. |
| 2006/0100604 | A1 | 5/2006 | Brenner et al. |
| 2006/0129090 | A1 | 6/2006 | Moberg et al. |
| 2008/0183153 | A1 | 7/2008 | Enns |
| 2008/0243085 | A1 | 10/2008 | Destefano |
| 2010/0076383 | A1 | 3/2010 | Bouphavichith et al. |
| 2010/0185159 | A1 | 7/2010 | Bagwell et al. |

FOREIGN PATENT DOCUMENTS

| | | |
|---|---|---|
| WO | WO 96/36378 A1 | 11/1996 |
| WO | WO 2004/091692 A2 | 10/2004 |
| WO | WO 2010/029853 A1 | 3/2010 |

*Primary Examiner* — Bhisma Mehta

(74) *Attorney, Agent, or Firm* — Karl V. Sidor

(57) ABSTRACT

A connector for coupling to a base of an indwelling device equipped with a circular hub having a radius, a top surface, a side surface, and a circumferential recess defined in the side surface. The connector has a resilient assembly including a plurality of release buttons extending from the resilient assembly and may include a conduit defining a fluid pathway through the connector. Each release button has a finger contact zone and a catch. The catch is configured to releasably engage the circumferential recess. The connector is coupled by positioning the connector on the circular hub and depressing the connector until the catches engage the circumferential recess such that the connector is configured to rotate completely about the circular hub. The connector is decoupled from the hub by pressing the release buttons to reversibly displace the respective catches radially to disengage from the circumferential recess.

17 Claims, 17 Drawing Sheets

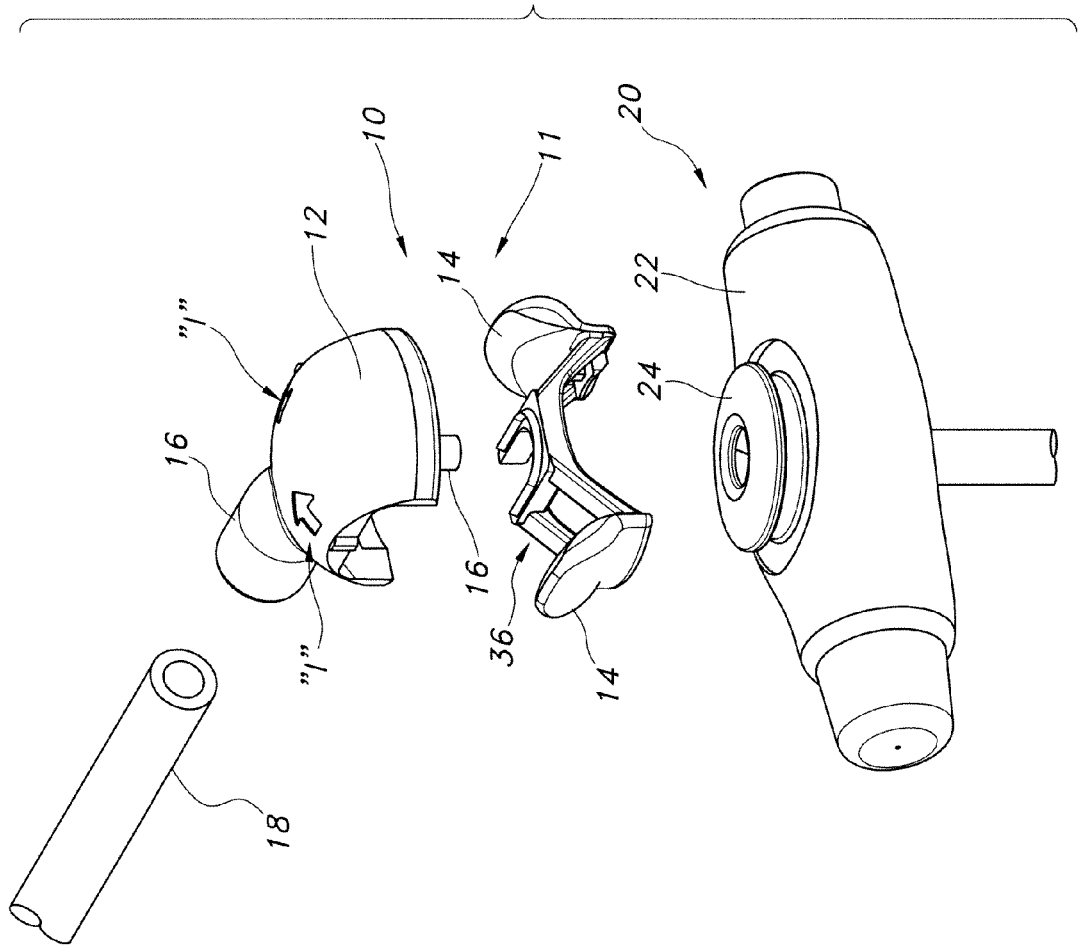

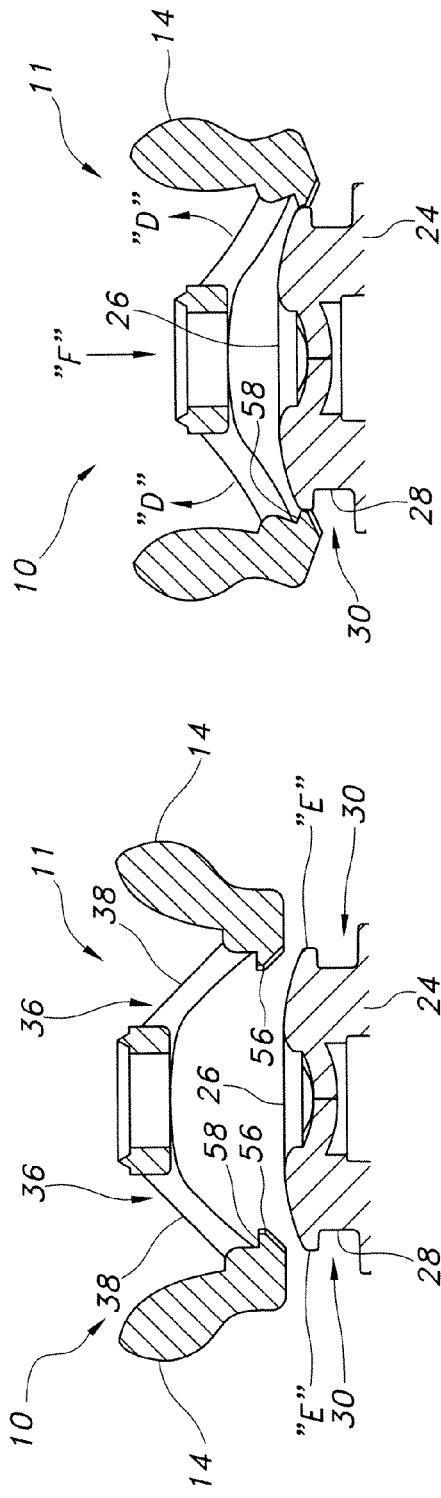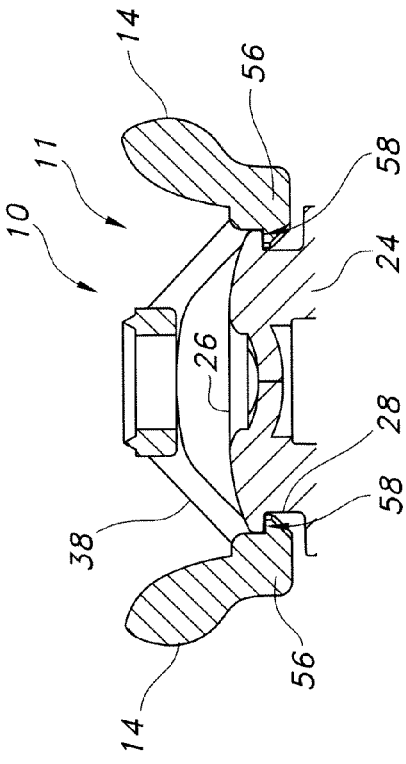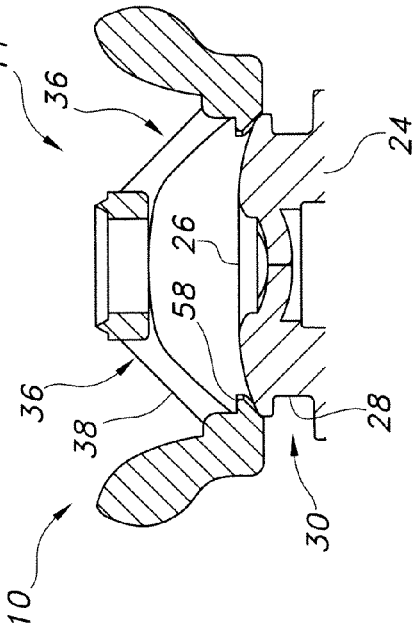
FIG. 7A  FIG. 7B  FIG. 7C  FIG. 7D

ENTERAL FEEDING EXTENSION SET CONNECTOR

This application claims the benefit of priority from U.S. Provisional Application No. 61/369,432, filed on Jul. 30, 2010, the contents of which are incorporated herein by reference.

FIELD OF THE INVENTION

The present invention relates to improved connectors that convey fluids from a supply tube to an indwelling tube or catheter. More particularly, it relates to an enteral feeding connector which joins a feeding extension set to an enteral feeding tube.

BACKGROUND

Numerous situations exist in which a body cavity needs to be catheterized to achieve a desired medical goal. One relatively common situation is to provide nutritional solutions or medicines directly into the stomach or intestines. A stoma is formed in the stomach or intestinal wall and a catheter is placed through the stoma. This surgical opening and/or the procedure to create the opening is common referred to as "gastrostomy". Feeding solutions can be injected through the catheter to provide nutrients directly to the stomach or intestines (known as enteral feeding). A variety of different catheters intended for enteral feeding have been developed over the years, including some having a "low profile" relative to the portion of the catheter which sits on a patient's skin, as well as those having the more traditional or non-low profile configuration. These percutaneous transconduit catheters (sometimes referred to as "percutaneous transconduit tubes") are frequently referred to as "gastrostomy catheters", "percutaneous gastrostomy catheters", "PEG catheters" or "enteral feeding catheters". U.S. Pat. No. 6,019,746 for a "Low Profile Balloon Feeding Device" issued to Picha et al. on Feb. 1, 2000, provides an example of one device.

The enteral feeding catheter serves as the pathway through the stoma for transconduit of feeding solution into the stomach or intestine. During feeding, the enteral feeding catheter must be connected to separate feeding tube that is associated with a pump that generates pressure to drive feeding solution from a reservoir through the feeding tube and into and through the enteral feeding catheter into the stomach or intestine. Feeding may take several hours and may occur at night while a patient is sleeping. Maintaining a robust and leak proof connection between the feeding tube and the enteral feeding catheter is important. It is also very desirable that the connection withstand twisting and pulling forces generated by movement of a patient.

However, a problem universal to low profile and non-low profile enteral feeding catheters is the difficulty in connecting and disconnecting the locking adapter of the feeding tube to and from the enteral feeding catheter base or head. Many prior art enteral feeding catheters, such as the one shown, for example, in cross-section in FIG. 1, have a low profile base B and a catheter C which extends through the base and a distance from the base. A distal end of the catheter of such a device/assembly often includes a balloon which may be expanded to hold the catheter in a position in a body lumen, such as a stomach lumen. Such an enteral feeding device/assembly also often has a plug "P" attached to the low profile or non-low profile device by a tether "T."

Connecting a feeding tube to conventional enteral feeding catheters requires removing the plug P from the base to allow access to the feeding passage opening. Conventional enteral feeding catheters are designed with a base or "head" having a locking cap member fitting in the feeding passage opening. The locking cap member is configured to receive a conventional locking adapter connected to the end of a feeding tube. Generally speaking, these locking cap members have a keyway, a groove, a stop member and incorporate a slot to provide a design that is similar to the female portion of a bayonet fitting. A locking adapter has a dispensing projection and a key portion attached to that projection that fit into the locking adapter. The locking adapter is pushed into the locking cap member and twisted in place until it locks. Exemplary illustrations of these conventional features may be found in the above referenced U.S. Pat. No. 6,019,746.

Connecting, changing and/or disconnecting a feeding tube having a conventional locking adapter to/from a conventional enteral feeding catheter can be a surprisingly difficult exercise. If the patient is overweight, his or her size can limit visibility of the enteral feeding catheter base from the patient so that the patient has to maneuver the locking adapter in or out of the enteral feeding catheter base by touch or feel rather than by sight. If the patient has impaired motor skills, fitting a lock adapter in the locking cap member presents challenges during the positioning, pushing and twisting steps. If the patient is young, it is often necessary or desirable to change the assembly while the patient is sleeping. The turning on of a light during the night can wake the patient. Yet, without being sure that the new tube is correctly connected, there is a risk of the leaking of gastric contents onto a patient's skin surface, clothing, and the like. There is also a similar risk of the leaking of the feeding solution. Further, when the connector sits tightly within the base, it may be difficult to remove, thereby requiring extensive pulling, movement of the connector and base and even unwanted displacement of the base, all of which can cause leakage or irritate a sensitive stoma site.

Some conventional locking adapters are configured to allow partial twisting or rotation after the adapter has been locked in place. That is, after the locking adapter is twisted in the locked cap member so the key portion travels past a "detent", the locking adapter can rotate between a position where the key portion contacts a stop and a position where the key portion contacts a detent. Unfortunately, the limited range of motion allows the conventional locking adapter to transmit twisting force to the enteral feeding catheter. This transfer of force may cause the catheter to twist or pull which can cause leakage or irritate a sensitive stoma site. If sufficient twisting force is inadvertently encountered, the key portion of the locking adapter may be forced past the detent as it would be when a patient or care give is disconnecting the locking adapter. After the key portion is forced past the detent, it can readily align with the slot/keyway thereby allowing the connector to inadvertently become completely disconnected. These conventional connectors have evident drawbacks that remain unresolved.

The popularity of low profile enteral feeding catheter heads or bases has also resulted in a low-profile conversion kit that provides a base or head component that is clamped onto a percutaneous transconduit catheter (i.e., only the tube) inserted through the abdominal wall using conventional endoscopic procedures or with a replacement percutaneous transconduit catheter (i.e., only the tube) that is inserted through a patient's stomach. Such a low-profile conversion kit is described in U.S. Pat. No. 5,549,657. According to that patent, base or head component has an anti-reflux valve assembly and a two-part clamp. After the base or head component is clamped on the end a percutaneous transconduit catheter, it functions as the base or head for the percutaneous transconduit catheter. The anti-reflux valve assembly includes a circular seat. A recess located beneath the seat is configured to receive opposed lips of a snap-fit feeding tube connector that snaps onto the circular seat. An example of such a low-profile conversion kit is commercially available as the Gaurderer Genie™ PEG System Kit available from Bard Nordic (Helsingborg, Sweden), a subsidiary of C.R. Bard Inc.

When a patient is ready to be fed, a snap-type feeding tube connector is snap fitted onto the anti-reflux valve assembly by pressing the snap-type feeding tube connector against the anti-reflux valve assembly to urge the lips of the feeding tube connector over the circular seat and into the recess located beneath the circular seat. When feeding is complete, the snap-type feeding tube connector is removed by prying or pulling on a set of opposed ears. Attachment and detachment of the feeding tube connector is facilitated by a set of opposed slots that enhances axial and radial distortion and flexure of snap-type connector when a force is applied to one or both of the opposed ears.

Connecting, changing and/or disconnecting a snap-type feeding tube connector to/from such a low-profile enteral feeding catheter head or base may also be a surprisingly difficult exercise at least for the same reasons as conventional locking adapter. Moreover, the application of force to press the snap-type feeding tube connector onto the head and also to pry it off the head transfers forces directly to the enteral feeding catheter which may create discomfort and cause irritation to the sensitive stoma site. The low-profile of the head and its relatively small size (e.g., typically between about 13 mm and 25 mm in diameter) also create difficulty in that opposed ears of the snap-type feeding tube connector can extend over the ends of the head and lie adjacent or even against the skin of the patient to make it difficult to grasp or pinch the ears between the fingers.

Accordingly, there is a need for a connector for coupling a medical fluid supply tube to the head of a catheter device having a circular hub. For example, there is a need for an enteral feeding extension set connector which permits a user or health care provider a way to easily connect and disconnect an extension set to the base of an enteral feeding tube. Such a system would permit a user or health care provider to easily and reliably disconnect the previous, used, feeding connector and connect a new feeding connector, desirably without needing to see the base.

SUMMARY

In response to the difficulties and problems discussed herein, the present invention provides a connector for coupling a medical fluid supply tube (e.g., a feeding extension set) to a base of a catheter device (e.g., an enteral feeding tube or enteral feeding catheter device) when the base is equipped with a circular hub having a radius, a top surface, a side surface, and a circumferential recess defined in the side surface. The connector is composed of a resilient assembly that may optionally include a cover or head. A plurality of release tabs or buttons (e.g., two or more release tabs or buttons) extends from the resilient assembly. The connector may also include a conduit defining a fluid pathway for transferring feeding solution from the feed extension tube to the lumen of the catheter device.

Generally speaking, each release tab or button has a first portion including a finger contact zone and a second portion including a catch. The catch is configured to releasably engage the circumferential recess defined in the side surface of the circular hub. The connector is coupled to the circular hub by positioning the connector on the circular hub and depressing the connector until the catches engage the circumferential recess defined in the side surface of the circular hub. The connector is decoupled from the hub by applying force (e.g., pressing) the release buttons to reversibly displace the respective catches radially to disengage from the circumferential recess. The release buttons may be resiliently biased by the resilient assembly. The resilient assembly contains at least one resilient member that may include cantilevered springs, compression springs, extension springs, resilient foams or the like and combinations thereof. In such configuration, the connector is decoupled from the hub by applying force (e.g., pressing) the release buttons to reversibly displace the resilient element (e.g., cantilever springs) thereby moving the respective catches radially to disengage from the circumferential recess.

The connector is rotatably coupled to the circular base on the base of the enteral feeding catheter device. That is, when coupled to the base of the enteral feeding catheter device, the connector may rotate completely about the circular hub in either direction of rotation without inadvertently decoupling from the enteral feeding catheter device or causing the enteral feeding catheter device to twist. Desirably, the connector will provide relatively little resistance to rotation so it may move readily in response to twisting or other forces to avoid kinking the feeding tube or transferring force to the catheter device.

In an aspect of the invention, the extension set connector may include a central support having an upper surface. The upper surface of the central support may form a distal portion of the connector. Cantilevered springs may extend radially outward from the central support, each spring having at least one arm, each arm having a first end, a central section, and a second end that is joined to the central support. The cantilevered springs may be compound cantilevered springs. It is contemplated that the cantilevered springs may be bridged together and connected by a cross-member to form the resilient assembly without the need for a central support. Alternatively, it is contemplated that the cantilevered springs and the head or cover of the connector such that the head or cover and the cantilevered springs are unitary.

The release buttons (also referred to as release tabs) are joined with the respective first ends of the cantilevered springs. The relationship between the cantilever springs and the release buttons may be characterized as a cantilevered structure in that the release button has one portion that is supported by the cantilevered spring and another portion that projects outwardly away from the resilient assembly. Each release button has a first portion with an exterior, outer or outward facing surface that forms or includes a finger contact zone. In addition, each release button has a second portion with an interior, inner or inward facing surface that forms or includes a catch on the inner surface. The catch is configured to releasably engage the circumferential recess defined in the side surface of the circular hub. Desirably, each catch may have a top surface configured to releasably engage the circumferential recess and a bottom surface and desirably the bottom surface is beveled.

The release button may desirably include a transition or delineation between the first portion and second portion. The second portion of the release button may also form a proximal portion of the connector; that is, the portion of the connector that is closest to the base when the connector is coupled to the base. The second portion of the release button may further include a boss adjacent the catch. Desirably, the boss slightly displaces the resilient assembly (e.g., the cantilevered springs of the resilient assembly) when the connector is coupled to the base. This displacement provides a tension or load the cantilevered springs that is transferred to the catches to hold the connector more securely to the circular hub.

The cantilever springs may be a pair of cantilever springs in opposed relationship and the release buttons may be a pair of release buttons. The pair of release buttons will also be in generally opposed relationship.

A conduit may define a fluid pathway through the connector and can be configured to supply a feeding solution to a lumen of the enteral feeding catheter device. The fluid pathway may be located between the pair of opposed cantilevered springs and the pair of release buttons. The fluid pathway may define a 90-degree bend such that the fluid pathway is generally perpendicular to the lumen of the enteral feeding catheter device. Alternatively, the fluid pathway may be configured to have the same orientation as the lumen of the enteral feeding catheter device. Such a configuration is desirable for delivering a bolus of feeding solution. The conduit may be in the form of a nozzle that is configured to engage an orifice defined in the hub to supply a feeding solution to a lumen of an enteral feeding catheter device. Alternatively, the conduit may be configured to engage a nozzle protruding from the surface of the hub to supply a feeding solution to the lumen of an enteral feeding catheter device.

The connector may further include motion limiters to limit the pitch of the connector. These motion limiters may be configured to contact an upper surface of the hub or an upper surface of the base of the enteral feeding catheter device. For example, the motion limiters may constitute a portion of the cantilever springs. The connector may also include a head joined to the central support. The head may form a distal portion of the connector. The head may also form a proximal portion of the connector. The motion limiters may be formed by a portion of the head and/or a proximal portion of the connector.

The present invention also encompasses an enteral feeding assembly. The enteral feeding assembly is composed of: (i) an enteral feeding catheter device having a base and including at least one catheter or tube with a lumen positioned through the base, the base having at least one circular hub having a radius, a top surface, a side surface and a circumferential recess defined in the side surface; and (ii) an extension set connector as generally described above for rotatably coupling a feeding extension set to a base of an enteral feeding catheter device wherein the connector allows for fluid communication between the feeding extension set and at least one lumen of the enteral feeding tube device.

The present invention further encompasses a feeding extension set. The feeding extension set includes a feeding extension tube and a connector in fluid communication with the enteral feeding extension tube, the connector configured for use with an enteral feeding catheter device having a circular hub. The connector has a plurality of release buttons incorporating catches. The connector is configured to rotatably couple to a circular hub by positioning the connector on a hub and pressing down on (e.g., depressing) the connector until the catches engage a circumferential recess defined in a side surface of a circular hub and the connector is further configured to decouple from a hub by squeezing or pinching the release buttons to move the respective catches radially to disengage from a circumferential recess.

BRIEF DESCRIPTION OF THE DRAWINGS

FIG. 4A is an exploded perspective view illustrating an exemplary enteral feeding catheter device equipped with a base having a circular hub and the extension set connector.

FIGS. 7A to 7D are side views illustrating a portion of an exemplary connector and a circular hub on the base of an enteral feeding catheter device in various stages of the process of coupling.

DETAILED DESCRIPTION

Figure 1:
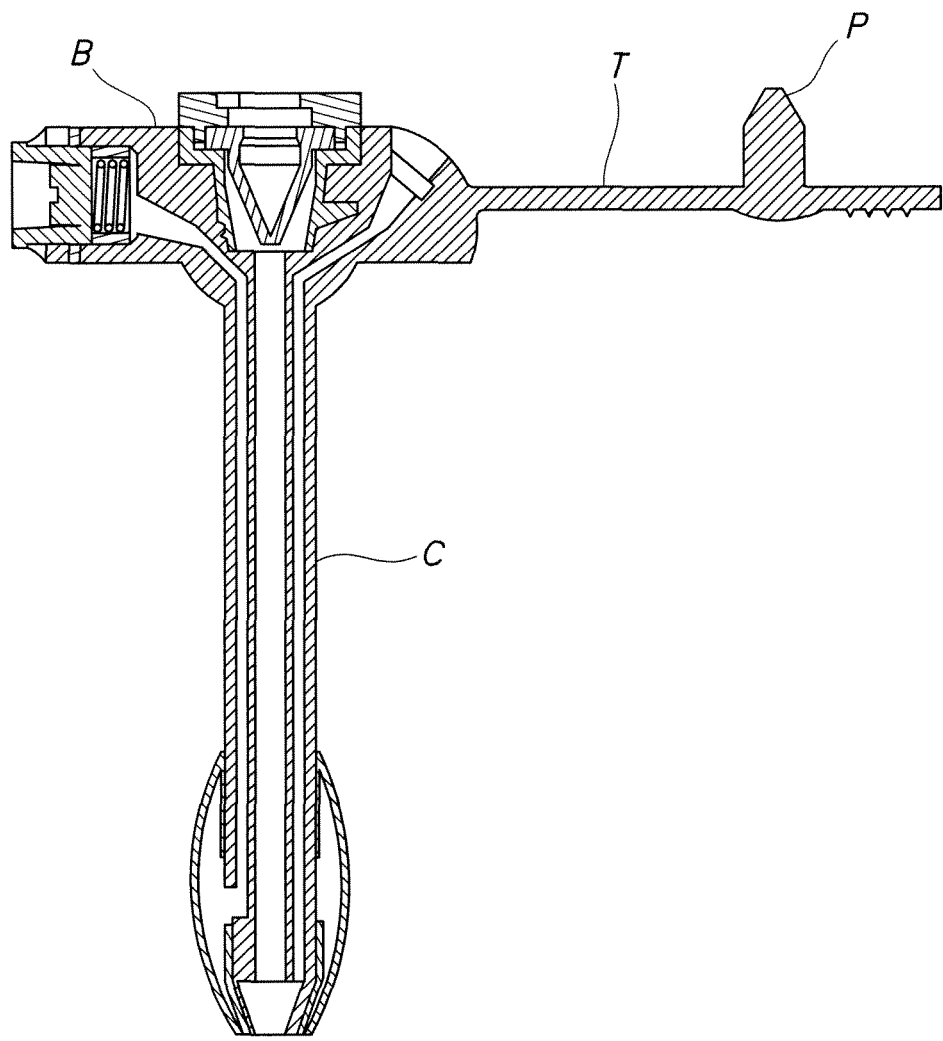
FIG. 1 is a side view of a prior art enteral feeding assembly, showing a base and attached catheter, and a plug used to close an opening which provides access to the catheter, the plug coupled to the base by a tether.

Reference will now be made in detail to one or more embodiments, examples of which are illustrated in the drawings. It should be understood that features illustrated or described as part of one embodiment may be used with another embodiment to yield still a further embodiment. It is intended that the claims include these and other modifications and variations as coming within the scope and spirit of the disclosure.

Figure 2:
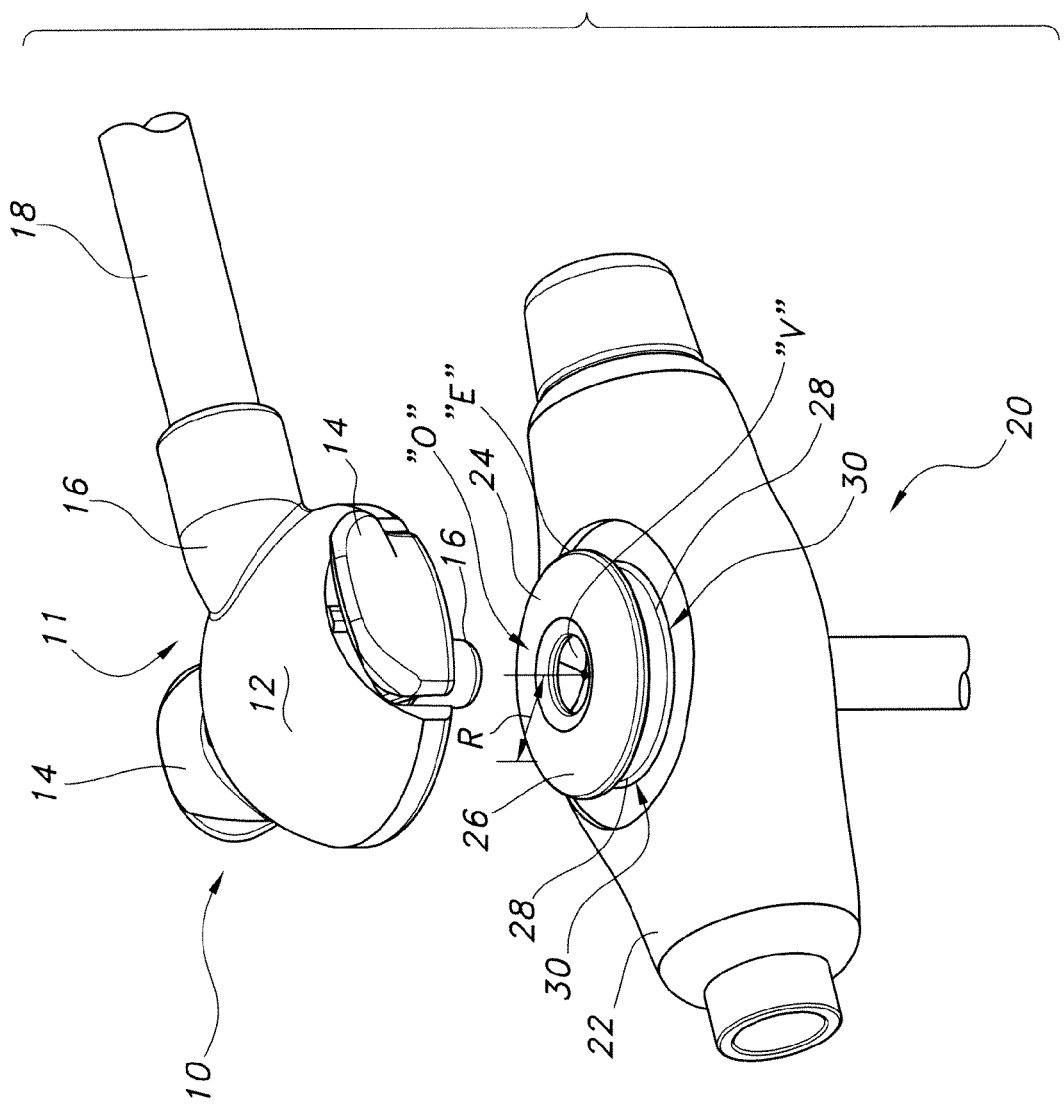
FIG. 2 is a perspective view illustrating an exemplary connector for coupling a feeding extension set to an enteral feeding catheter device having a circular hub.

Turning now to the drawings, it will be understood that an example of the prior art is illustrated in FIG. 1 and has been described above. FIG. 2 of the drawings is a perspective view illustrating an exemplary connector for coupling a medical fluid supply tube (e.g., feeding extension set) to a base of a catheter device (e.g., an enteral feeding catheter device) having a circular hub. As used herein, the term "fluid" encompasses liquids, gases and combinations thereof. An example of a liquid includes nutritional liquids that may be supplied to a patient through a feeding tube. An example of a gas may be a gas vented from the stomach or intestine of a patient. The connector 10 (referred to hereinafter as an "extension set connector") has a resilient assembly 11 that may optionally include a cover or head 12. The connector 10 also includes a plurality of release buttons 14 (e.g., two or more release buttons which may also referred to as tabs, projections, tongues, etc.) extending from the resilient assembly 11. The connector may also include a conduit 16 defining a fluid pathway for transferring feeding solution from the feed extension tube 18 to the lumen of an enteral feeding catheter device 20.

The extension set connector 10 is shown in position above an enteral feeding catheter device 20 that is equipped with a base 22 having a circular hub 24. The circular hub has a radius "R", a top surface 26, a side surface 28, and a circumferential recess 30 defined in the side surface 28. In other words, the circular hub 24 has a generally horizontal top surface 26 that extends over a generally vertical side surface 28 forming rim, collar, rib or flange structure that defines a circumferential recess 30 which is sized to engage the catches 56 of the connector 10. The radius "R" is the distance from the center of the hub 24 to the outermost edge "E" of the portion of the top surface 26 forming the rim, collar, rib or flange structure that defines the recess 30. The circular hub 24 also includes an orifice "O" at the center of the hub. A valve "V" is desirably used to seal the orifice "O" when the connector 10 is not engaged with the circular hub 24.

Generally speaking, each release button has a first portion including a finger contact zone and a second portion including a catch, described in more detail below. The catch is configured to releasably engage the circumferential recess 30 defined in the side surface 28 of the circular hub 24. The connector 10 is coupled to the circular hub 24 by positioning the connector 10 on the circular hub 24 and depressing the connector until the catches engage the circumferential recess defined in the side surface of the circular hub. Of course, the connector 10 may be coupled to the circular hub 24 by squeezing or pinching the release buttons 14 between the fingers so the catches 56 clear the outermost edge "E" of the top surface forming the rim, collar, rib or flange structure 30, seating the connector 10 on the circular hub 24 and releasing the squeezing or pinching force on the release buttons so the catches 56 engage the circumferential recess 30. The connector is decoupled from the hub by pressing (e.g., squeezing or pinching) the release buttons to reversibly displace the respective catches radially (e.g., radially outward) to disengage from the circumferential recess. Desirably, the connector is rotatably coupled to the circular base on the base of the enteral feeding catheter device. That is, the connector may rotate completely about the circular hub in either direction of rotation without disconnecting from the enteral feeding catheter device or causing the enteral feeding catheter device to twist. It is desirable for the connector to be rotatably coupled such that it can rotate freely around the circular hub with relatively little resistance.

The release buttons may be resiliently biased by the resilient assembly 11. The resilient assembly contains at least one resilient member that may include cantilevered springs, compression springs, resilient foams or the like and combinations thereof. If the resilient assembly 11 includes cantilevered springs, each cantilevered spring has at least one arm. Each arm has a first end, a central section, and a second end that is joined to a central support. In such configuration, the connector is decoupled from the hub by depressing the release buttons to reversibly displace the resilient element (e.g., cantilever springs) thereby moving the respective catches radially (e.g., radially outward) to disengage from the circumferential recess.

Figure 3A:
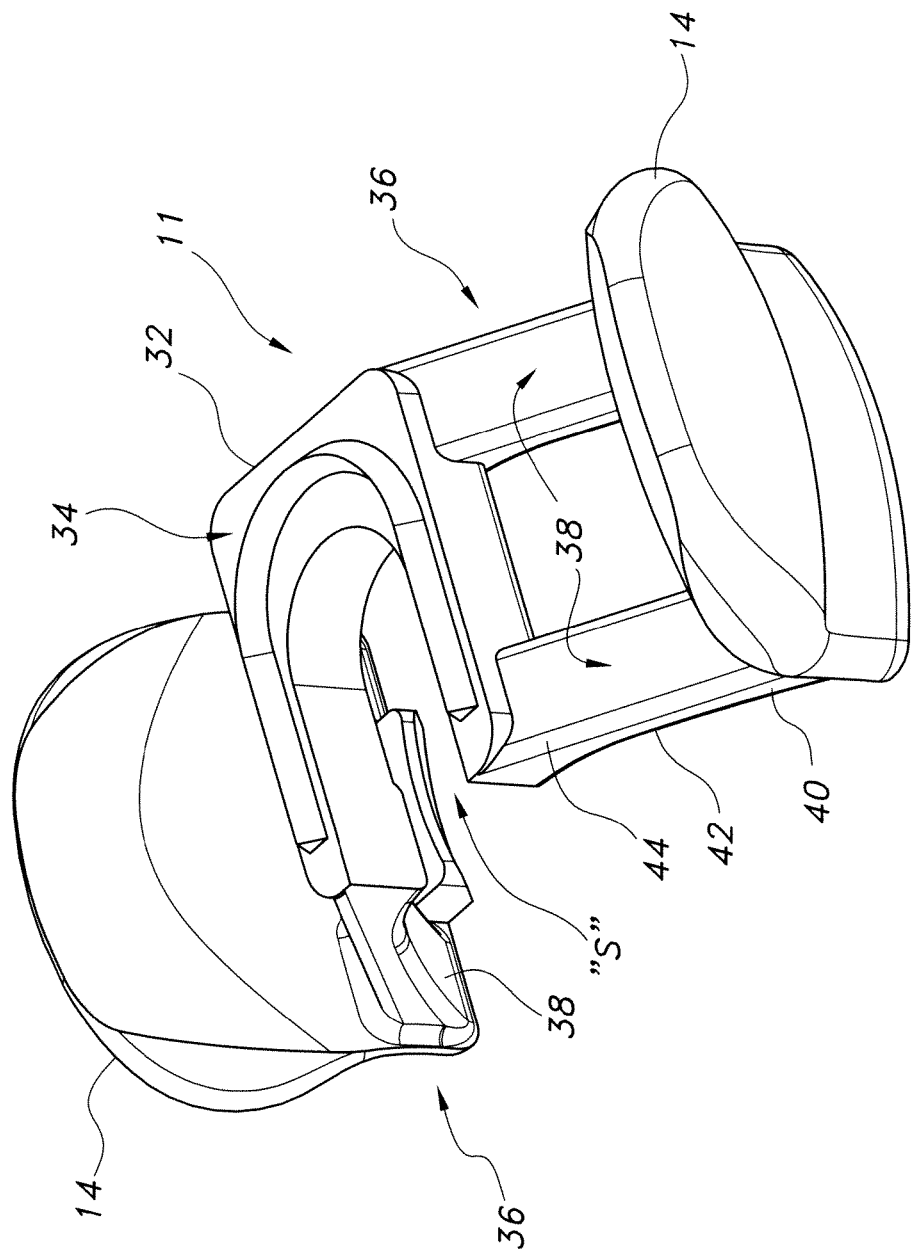
FIG. 3A is perspective view illustrating a detail of a portion of an exemplary extension set connector.

Referring now to FIG. 3A of the drawings, there is shown in perspective view an illustration detailing of a portion of an exemplary connector. More particularly, FIG. 3A illustrates a portion of an exemplary resilient assembly 11 for resiliently biasing the release buttons. The resilient assembly 11 desirably includes a central support 32 having an upper surface 34. The upper surface 34 of the central support 32 may form a distal portion of the connector. That is, the upper surface may form the portion of the connector that is farthest from the enteral feeding catheter device 20. The portion of the resilient assembly 11 also includes cantilevered springs 36 extending radially outward from the central support 32, each cantilevered spring 36 may have at least one arm 38. Each arm 38 has a first end 40, a central section 42, and a second end 44 that is joined to the central support 32. The cantilevered springs 38 may be compound cantilevered springs. Release buttons 14 are engaged with the resilient assembly 11 by being joined with the respective first end 40 of a cantilevered spring 36. The relationship between the cantilever spring and the release button may be characterized as a cantilevered structure in that the release button has one portion that is supported by the cantilevered spring and another portion that projects outwardly away from the resilient assembly. While FIG. 3A illustrates the cantilever springs as two pairs of cantilever springs in opposed relationship and the release buttons as a pair of release buttons that are also configured in opposed relationship, it is contemplated that other configurations may be used. For example, three cantilevered springs (or more) and three release buttons (or more) may be used and can be configured to be operated by three fingers (e.g., thumb, index finger and middle finger) or various combinations of more fingers.

Figure 3B:
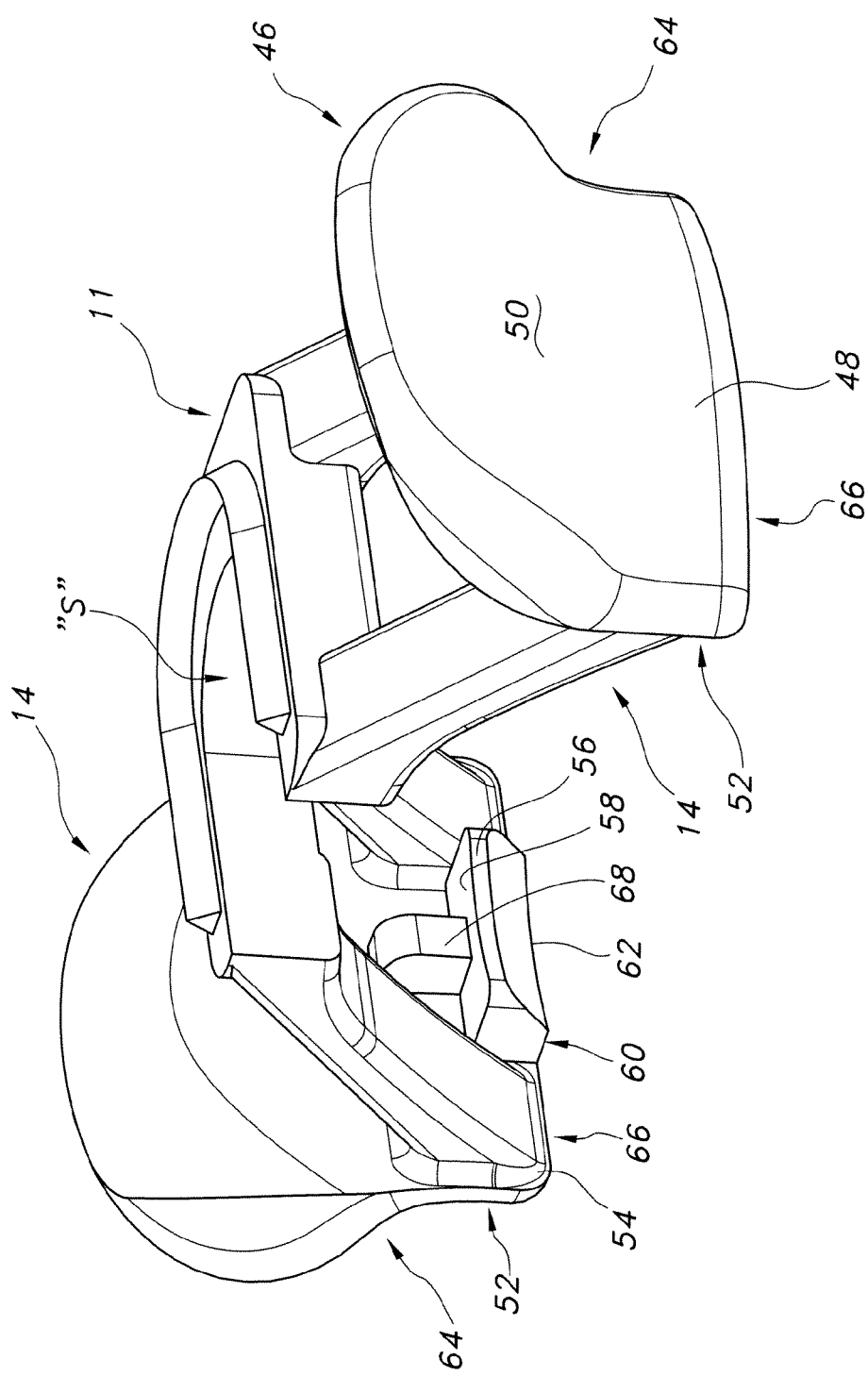
FIG. 3B is a perspective view illustrating a detail of a portion of an exemplary extension set connector which highlights the release buttons.
Figure 3C:
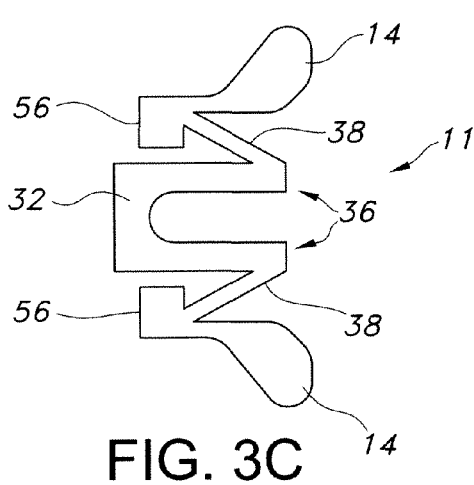
FIGS. 3C to 3E are top view illustrations of variations of the resilient assembly.

Referring now to FIG. 3B of the drawings, there is shown in perspective view an illustration which highlights a detail of a portion of the resilient assembly 11 and the release buttons 14. Each release button 14 has a first portion 46 with an exterior, outer or outward facing surface 48 that forms or includes a finger contact zone 50. In addition, each release button has a second portion 52 with an interior, inner or inward facing surface 54 that forms or includes a catch 56 on the inner surface 54. The catch 56 is configured to releasably engage the circumferential recess 30 defined in the side surface 28 of the circular hub 24. Desirably, each catch 56 may have a top surface 58. The top surface 58 is configured to releasably engage an underside (not shown) of the generally horizontal top surface 26 that extends over the generally vertical side surface 28 forming rim, collar, rib or flange structure that defines the circumferential recess. Each catch may also have a bottom surface 60. Desirably, a portion of the bottom surface 60 may have a bevel 62. The bevel 62 can be adjusted to provide an angle sufficient to allow for easier attachment when the connector 10 is pressed downward against the circular hub 24 to avoid applying a level of force that creates discomfort and causes irritation to the sensitive stoma site.

Figure 4B:
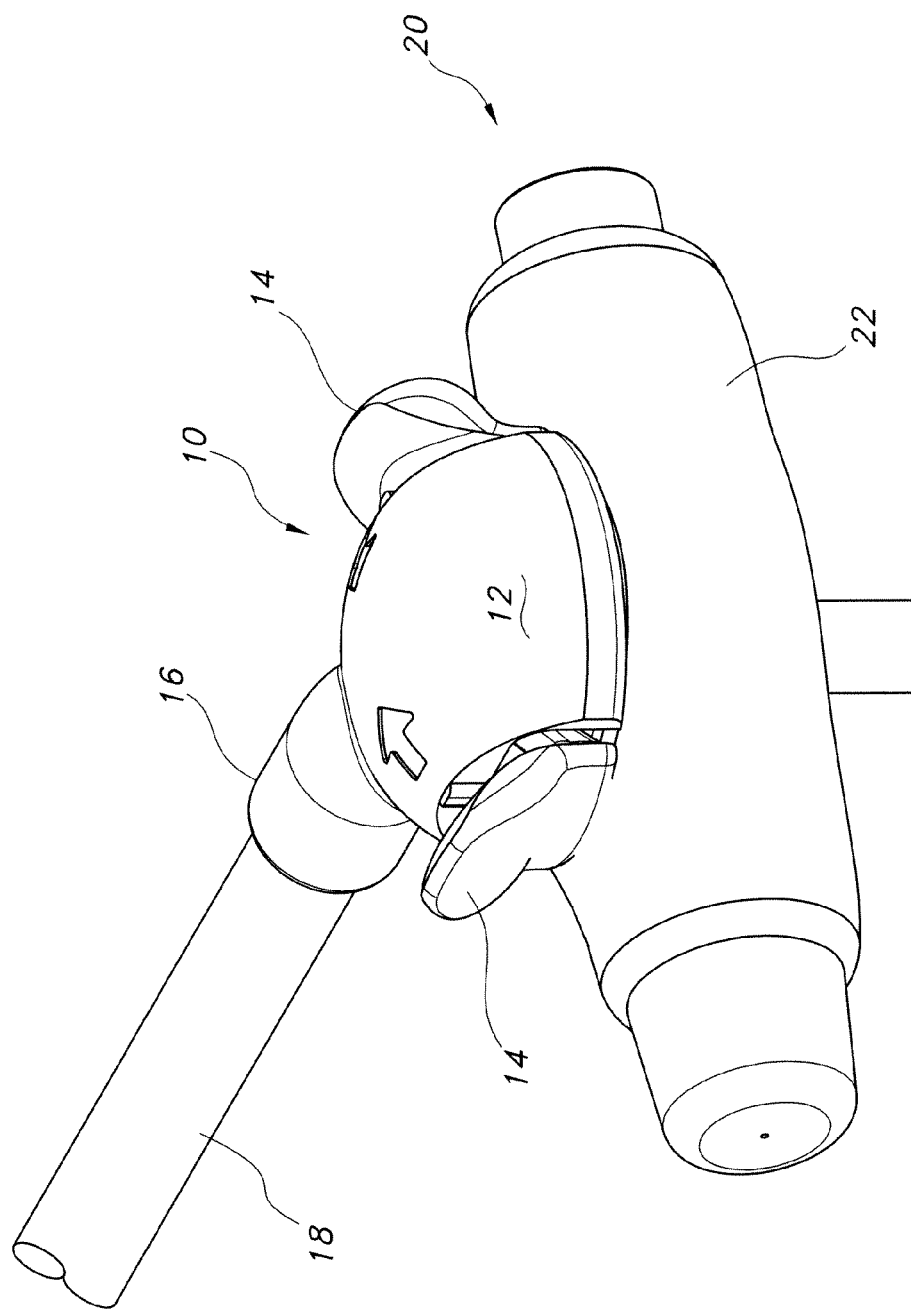
FIG. 4B is a perspective view illustrating the components shown in FIG. 4A as they would appear when a connector is coupled to the circular hub on the base of the enteral feeding catheter device.
Figure 13:
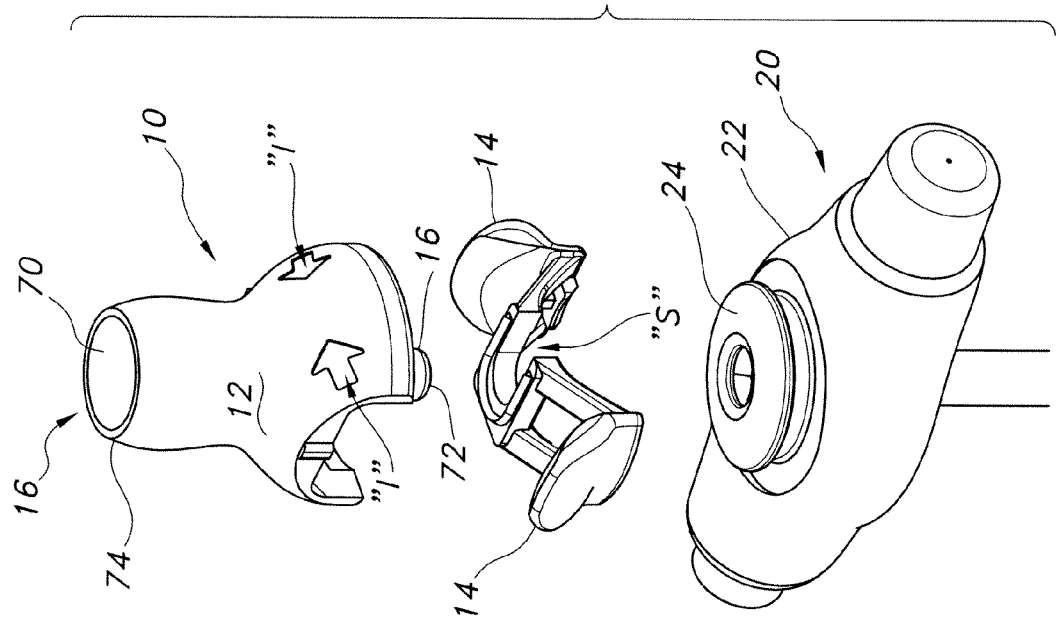
FIG. 13 a partial exploded perspective view illustrating an extension set connector in which both a proximal end and a distal end of a conduit a defining a fluid pathway is axially aligned with the lumen of an enteral feeding catheter device.

The release button 14 may desirably include an optional transition or delineation 64 between the first portion 46 and the second portion 52. This transition 64 helps define the finger contact zone 50. The finger contact zone 50 is illustrated in FIG. 3B as generally smooth. The finger contact zone 50 may have topography to help the users identify the finger contact zone 50 through visual and/or tactile indicia such as, for example, bands, bumps, ridges, raised dots, random rough texture, contracting color or the like. Alternatively and/or additionally, the cover or head 12 of the extension set connector 10 may include indicia "I" as illustrated in FIGS. 4A, 4B as well as FIGS. 13 and 14. These indicia "I" may be used to provide a tactile or visual cue to a user about the location of the release buttons and/or the direction to press squeeze or pinch the release buttons.

In an aspect of the invention, the second portion 52 of the release button may form a proximal portion of the connector 10 (i.e., the portion of the connector (excluding any projecting nozzle or conduit) that is oriented toward and generally positioned closest to the exterior surface of base 22 of the enteral feeding catheter device 20). For example, the bottom face 66 of the second portion 52 of the release button 14 may form the proximal portions of connector 10. As another example, the bottom face 66 of the second portion of the release button 14 and the bottom surface 60 of the catch 56 may form proximal portions of the connector 10. In another aspect of the invention, the second portion 52 of the release button 14 may further include a boss 68 adjacent the catch 56. The purpose of the boss 68 is to slightly displace the resilient assembly (e.g., the cantilevered springs of the resilient assembly) when the connector is coupled to the base. This displacement provides a tension or load to the cantilevered spring 36 that is transferred to the catches 56 to secure the connector 10 to the circular hub so it does not wobble or rattle, yet is able to rotate in response to a relatively low level of force.

Figure 3D:
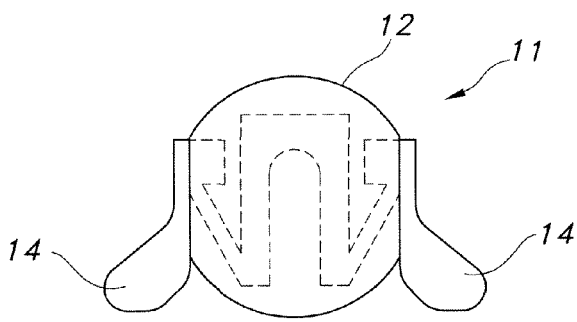
Figure 3E:
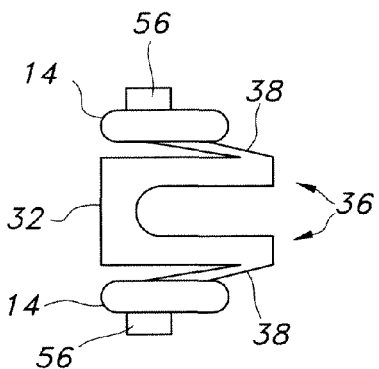

FIGS. 3C through 3I are illustrations of alternate variations of the resilient assembly and release buttons as well as variations of the circular hub 24. In one example shown by top view illustration in FIG. 3C, the resilient assembly 11 may include cantilevered springs arranged so they are oriented generally parallel with the top surface 26 of the circular hub 24. FIG. 3D is a top view illustration of the resilient assembly 11 joined with the head or cover 12. As can be seen, the release buttons 14 extend radially outward so that squeezing or pinching the release buttons between two fingers displaces the catches 56 radially outward and removing the pinching or squeezing force allows the catches 56 to move radially inward. FIG. 3E is a top view illustration of the resilient assembly 11 with cantilevered springs arranged so they are oriented generally parallel with the top surface 26 of the circular hub 24 and in which the release buttons 14 and catches are configured so that pinching or squeezing the release buttons 14 between two fingers flexes the cantilevered springs so the catches 56 are displaced radially inward and removing the pinching or squeezing force allows the catches to move radially outward. Such a configuration illustrated in FIG. 3E is useful for an alternative version of a circular hub as illustrated in cross-sectional view in FIG. 3F. As can be seen, the hub 24 is in the form of a ring or circular band 100 projecting from the base 22 of the enteral feeding device.

Figure 3F:
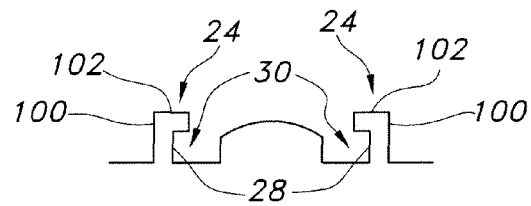
FIGS. 3F and 3G are side cross-sectional view illustrations of variations of the circular hub.
Figure 3G:
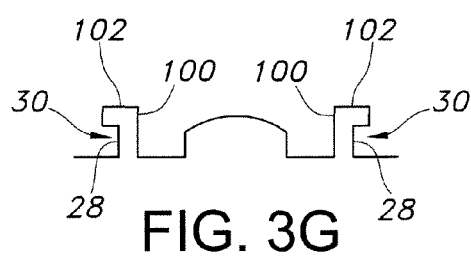
Figure 3H:
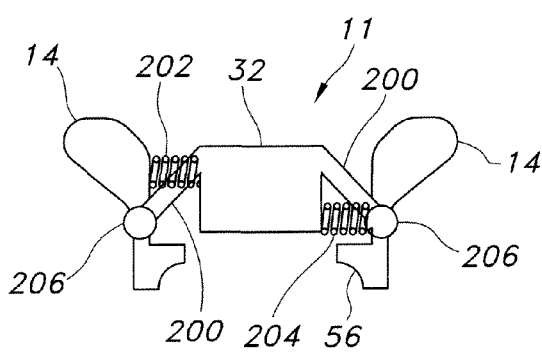
FIG. 3H is a side view illustration of a variation of the resilient assembly.
Figure 3I:
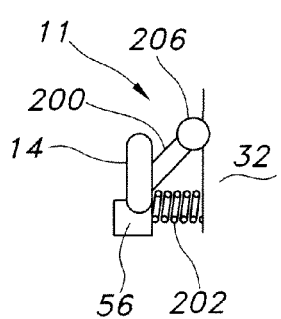
FIG. 3I is a top view illustration of a variation of the resilient assembly.

The band 100 has top surface 102 and a side 28. The projection or overlap of the top surface 102 over the side defines a recess 30. The top surface 102 may project over the side in a radially inward direction to define a recess as shown in FIG. 3F or it may project in a radially outward direction to define a recess as shown in FIG. 3G According to an aspect of the invention, the release buttons may be joined to arms or elements that are inflexible or relatively rigid unlike the cantilevered springs. Referring now to FIGS. 3H and 3I, it is contemplated that the release buttons 14 may be joined to inflexible arms 200 that are attached to the central support 32 or directly to the head or cover 12 utilizing a pivot connector 206, a living hinge or the like. A spring or resilient material such as foam can be used to provide the radial force to urge the release buttons 14 and their respective catches 56 in the desired direction. For example, one end of an extension spring 204 (or resilient foam or the like) may be joined to the central support 32 or to the head or cover 12 and the other end may be joined to a portion of the arm 200 or to the release button 14 itself so that the extension spring 204 provides a radially directed force that resiliently biases the second portion the release buttons (including the catches) in a radial direction—in this example in the radially inward direction (i.e., toward the center of the resilient assembly 11). Alternatively and/or additionally, it is contemplated that one end of a compression spring 202 (or resilient foam or the like) may be joined to the central support 32 or to the head or cover 12 and the other end may be joined to a portion of the arm 200 or to the release button 14 itself so that the compression spring 202 provides a radially directed force that resiliently biases the second portion the release buttons (including the catches) in radial direction—in this example in the radially outward direction (i.e., away from the center of the resilient assembly 11). FIG. 3I is a top view illustration showing an exemplary arm 200 arranged so it is oriented generally parallel with the top surface 26 of the circular hub 24. One end of a compression spring 202 is joined to the central support 32 (or to the head or cover 12) and the other end of the compression spring is joined a portion of the arm 200 or to the release button 14. As can be seen in the illustration, the release button 14 and catch 56 are configured so that pinching or squeezing a pair of the release buttons mounted on arms in this manner between two fingers would displace the arms 200 and release buttons so the catches are displaced radially inward and removing the pinching or squeezing force allows the catches to move radially outward.

FIG. 4A is an exploded perspective view showing the relationship between the enteral feeding catheter device 20 equipped with a base 22 having a circular hub 24 and the extension set connector 10 including a resilient assembly 11 with an optional cover or head 12. As can be seen in this configuration, the head or cover 12 may be formed separately from the resilient assembly 11. In other configurations, the resilient assembly 11 may be one in which the cantilever springs, central support, and the head or cover are integrated or formed as a unitary component. The conduit 16 provides a passage for transferring feeding solution from the feed extension tube 18 through the connector 10 and into the base 22 of the enteral feeding device 20. FIG. 4B is perspective view of the components shown in FIG. 4A as they would appear when the connector 10 is coupled to the circular hub 24 on the base 22 of the enteral feeding catheter device 20.

Figure 5:
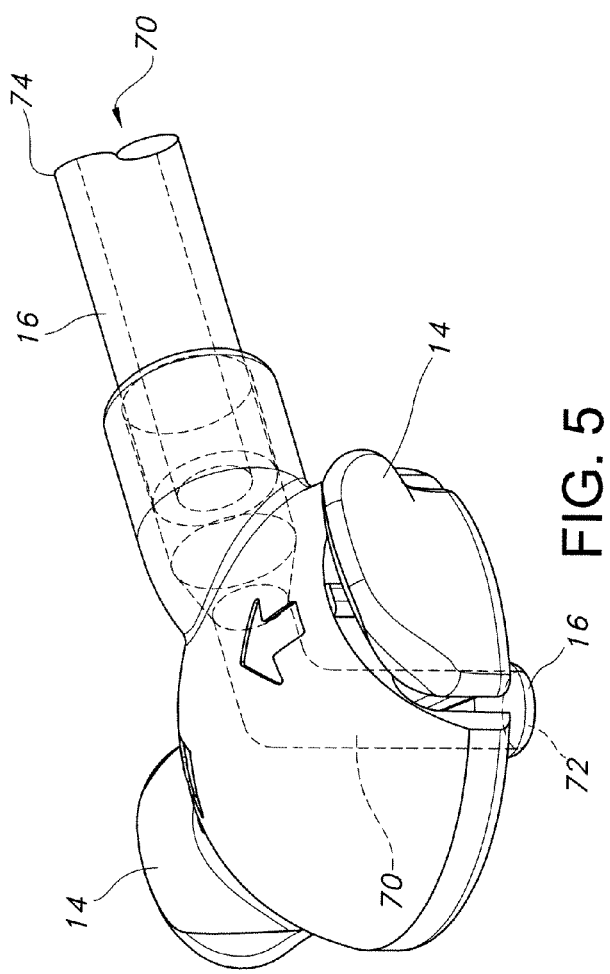
FIG. 5 is a perspective view illustrating a detail an exemplary extension set connector including a conduit.
Figure 6:
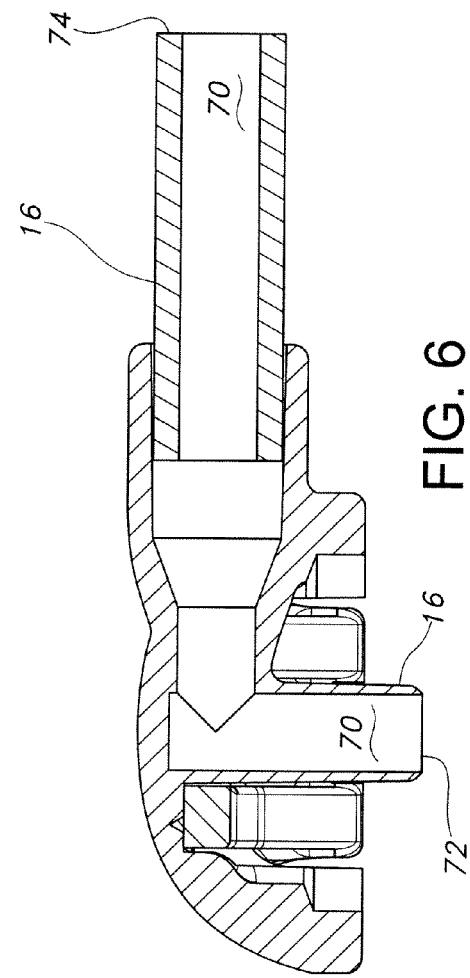
FIG. 6 is a cross-sectional view illustrating a detail an exemplary extension set connector including a conduit.
Figure 14:
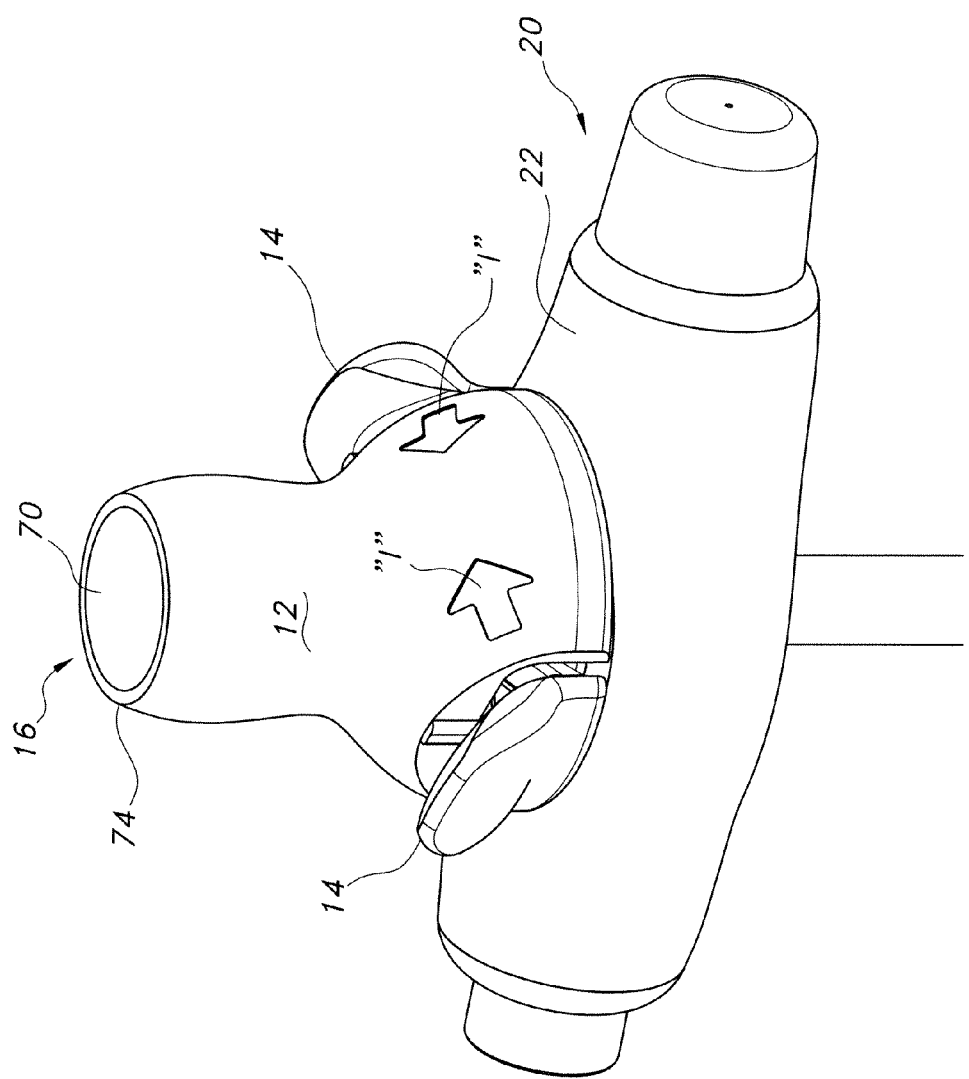
FIG. 14 is a side perspective view showing the extension set connector of FIG. 13 engaged with the base of an enteral feeding catheter device.

Referring now to FIGS. 5 and 6, FIG. 5 shows a perspective view of a connector 10 including a conduit 16 defining a fluid pathway 70 through the connector and FIG. 6 shows a cross-sectional view of a connector 10 including a conduit 16 defining a fluid pathway 70 through the connector. The conduit 16 is configured to supply a feeding solution to a lumen of the enteral feeding catheter device. In some embodiments, the conduit 16 defining the fluid pathway 70 may be located in a space "S" defined by the central support 32 between the pair of opposed cantilevered springs and the pair of release buttons as generally illustrated in FIGS. 3 and 4. A proximal end 72 of the conduit 16 defining the fluid pathway may be axially aligned with the lumen of the enteral feeding catheter device and then may have a 90 degree bend such that the distal end 74 of the conduit extends in a generally perpendicular manner to proximal end. This configuration is useful for most feeding applications. Alternatively, the proximal end 72 of the conduit 16 defining the fluid pathway may be axially aligned with the lumen of the enteral feeding catheter device and then may continue such that the distal end 74 of the conduit extends continues in an axially aligned manner to proximal end as illustrated in exploded perspective view in FIG. 13. Such a configuration is desirable for delivery of a bolus of feeding solution. FIG. 14 is a side perspective view showing the extension set connector 10 of FIG. 13 coupled with the base 22 of an enteral feeding catheter device 20.

The conduit 16 may be in the form of a nozzle as generally illustrated in FIGS. 2, 5 and 6 that is configured to extend past the proximal end of the connector to engage an orifice "O" defined in the hub 24 to supply a feeding solution to a lumen of an enteral feeding catheter device. Alternatively, the conduit 16 may be configured to engage a nozzle (not shown) protruding from the surface of the hub to supply a feeding solution.

FIGS. 7A to 7D of the drawings are a series of illustrations showing a side view of a portion of an exemplary connector 10 composed of the resilient assembly 11 and the release buttons 14 as they interact with the circular hub 24 in various stages of the process of coupling or connection. FIG. 7A illustrates the connector 10 is positioned directly over the circular hub 24. FIG. 7B illustrates the connector initially contacting the circular hub 24 as it is depressed onto the circular hub. FIG. 7C illustrates the arms 38 of the cantilevered springs 36 providing a resilient bias to the release buttons 14 such that the release buttons 14 readily deflect (illustrated by arrows "D") as the downward pressure or force (illustrated by arrow "F") is applied to the connector allowing the catches 56 to slide past the edge of the circular hub. FIG. 7D illustrates the catches 56 engaged in the circumferential recess 30 defined in the side surface 28 of the hub 24 to couple the connector to the circular hub 24 on the base of an enteral feeding catheter device. The top surface 58 is configured to releasably engage an underside (not shown) of the generally horizontal top surface 26 that extends over the generally vertical side surface 28 forming rim, collar, rib or flange structure that defines the circumferential recess.

The downward force needed to accomplish the coupling is generally less than about 10 Newtons and is desirably between about 0.1 Newtons and 8 Newtons. Such a low level of force is very important because the downward force is transferred directly to the enteral feeding catheter device which resides in the sensitive stoma site. This configuration avoids much higher levels of forces required to snap a snap-type connector into place. For example the downward force needed to snap a snap-type connector into place is generally much greater. This is very important because the present invention avoids irritating the sensitive stoma site and the low level of force used to engage the connector helps patients that are mobility impaired, sight impaired, or who otherwise have difficulty seeing or reaching the feeding device (e.g., obese patients, patients with poor motor skills, etc.).

The cantilevered springs and release buttons also provide a positive tactile signal when the catches 56 slide into the circumferential recess 30 defined in the side surface 28 of the hub. The cantilevered springs provide increasing resistance as the release buttons deflect while the connector is depressed onto the hub. The resistance immediately dissipates when the catches enter the recess to provide a tactile signal. This action also produces an audible signal that may be characterized as a "snap" or "click" to alert the user that the catches are engaged in the recess. These tactile and audible signals are very important for users and care providers to know that a proper and secure connection is made.

Figure 8:
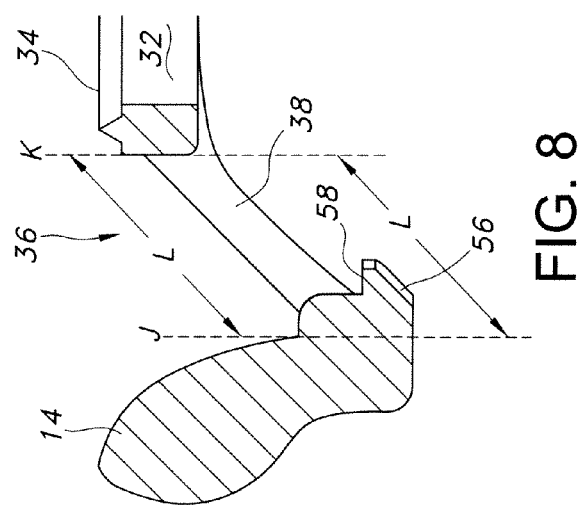
FIG. 8 is a side view illustrating a feature of an example connector highlighting a portion of an exemplary cantilevered spring.

FIG. 8 is a side view illustrating the general locations for determining the length "L" of the arm 38 of a cantilevered spring 36 by measuring the distance between the locations of the connections at each end of the arm(s) 38 of the spring 36. The location of the connection between the arm 38 and the release button 14 is shown by a broken line "J". Similarly, the location of the connection between the arm 38 and the central support 32 is shown by a broken line "K" in FIG. 8. While it is contemplated that various geometries, tapers or connection configurations may be used in the construction of the arm and/or between the arm and the release button and/or the central support, the length measurement is intended to be straightforward and determined as the distance between the two connections. If differences exist between the lengths of the upper and lower surfaces of the arm 38, an average of the two lengths may be used. If a compound cantilevered spring is used, the length measurement is determined by measuring the distance between the two connections. While it is contemplated that configurations may be used that result in varying lengths for opposed cantilevered springs, it is thought to be desirable for the length of each opposed cantilevered spring to be equal otherwise an imbalance in performance or force would occur. In situations where a cantilevered spring 26 has multiple arms 38 as illustrated in FIGS. 3 and 4 and differences exist between the lengths of these arms, an average of the two lengths may be used Each arm 38 of a cantilevered spring 36 may have a length "L" measured from its connection with the release button 14 to its connection with the central support that is from about 0.75 to about 1.25 times the length of the radius of the circular hub. For example, each arm 38 of a cantilevered spring 36 may have a length measured from its connection with the release button 14 to it connection with the central support 32 that is from about 0.85 to about 1.15 times the length of the radius of the circular hub. As another example, each arm may have a length that is from about 0.9 to about 1.10 times the length of the radius of the circular hub. While the inventors should not be held to any specific theory of operation, the specified ratio between the length of each arm 38 and the radius "R" of the circular hub 24 is thought to provide a length sufficient for the arm(s) of the cantilevered spring (when made of suitable plastic or other material including, but not limited to, nylon, polycarbonate, polyurethane, or the like) to deflect enough to allow coupling and decoupling of the connector at the predetermined levels of force and without causing premature fatigue of the materials in the spring. Generally speaking, the radius of the circular hub may range from about 0.75 inch to about 0.12 inch (~19 mm to 3 mm). For example, the radius of the circular hub may range from about 0.66 inch to about 0.25 inch (~17 mm to 6 mm). As another example, the radius of the circular hub may be from about 0.5 inch to about 0.33 inch (~13 mm to ~8 mm).

Figure 9A:
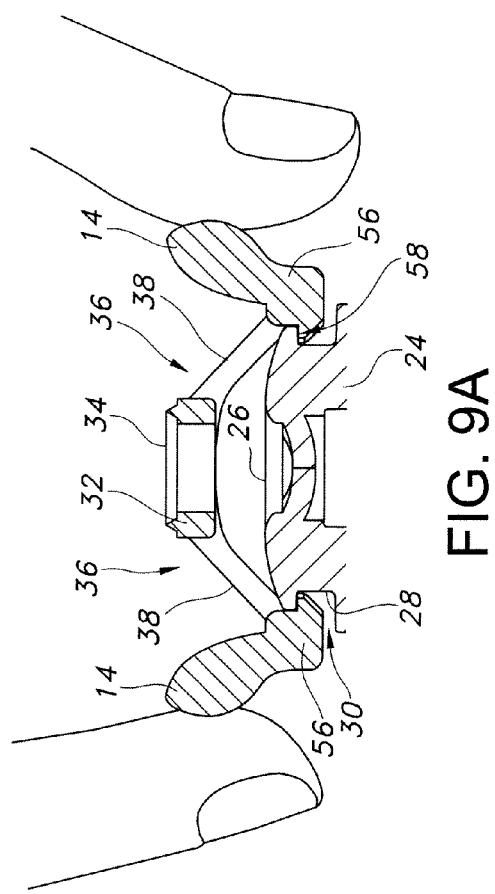
FIGS. 9A and 9B are side views illustrating a portion of an exemplary connector and a circular hub on the base of an enteral feeding catheter device in various stages of the process of decoupling.
Figure 9B:
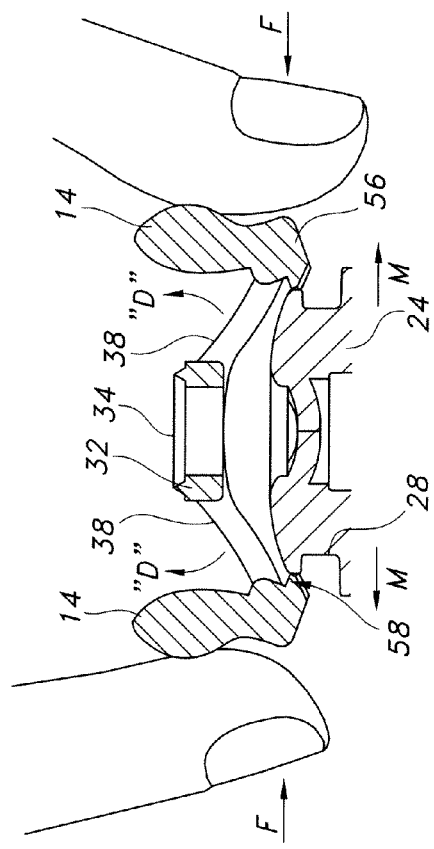

According to the invention, the connector 10 is decoupled from the circular hub 24 by depressing the release buttons 14 to reversibly displace the respective catches 56 radially outward to disengage from the circumferential recess 30. When the release buttons 14 are resiliently biased by cantilevered springs 36, the arms 38 of the cantilevered springs are reversibly displaced when a force is applied to their respective release buttons 14 at the finger contact zone 50 as generally illustrated in FIGS. 9A and 9B. By squeezing or pinching the release buttons 14 between two fingers, a force "F" is directed radially inward toward the central support. The force is translated into a torque or rotational force that deflects "D" the arms 38 and moves "M" the respective catches 56 radially outward away from the central support 32 to disengage the circumferential recess 30 defined in the side surface 28 of the circular hub 24. For example, each arm 38 of the cantilever spring 36 desirably is reversibly displaced by a force of between about 2 and about 14 Newtons applied to its respective release button. As another example, each arm of the cantilever spring desirably is reversibly displaced by a force of between about 4 and about 12 Newtons applied to its respective release button at the finger contact zone radially inward (e.g., toward the central support or the center of the connector). As another example, each arm of the cantilever spring desirably is reversibly displaced by a force of between about 6 and about 8 Newtons applied to its respective release button at the finger contact zone radially inward (e.g., toward the central support or the center of the connector).

Figure 10:
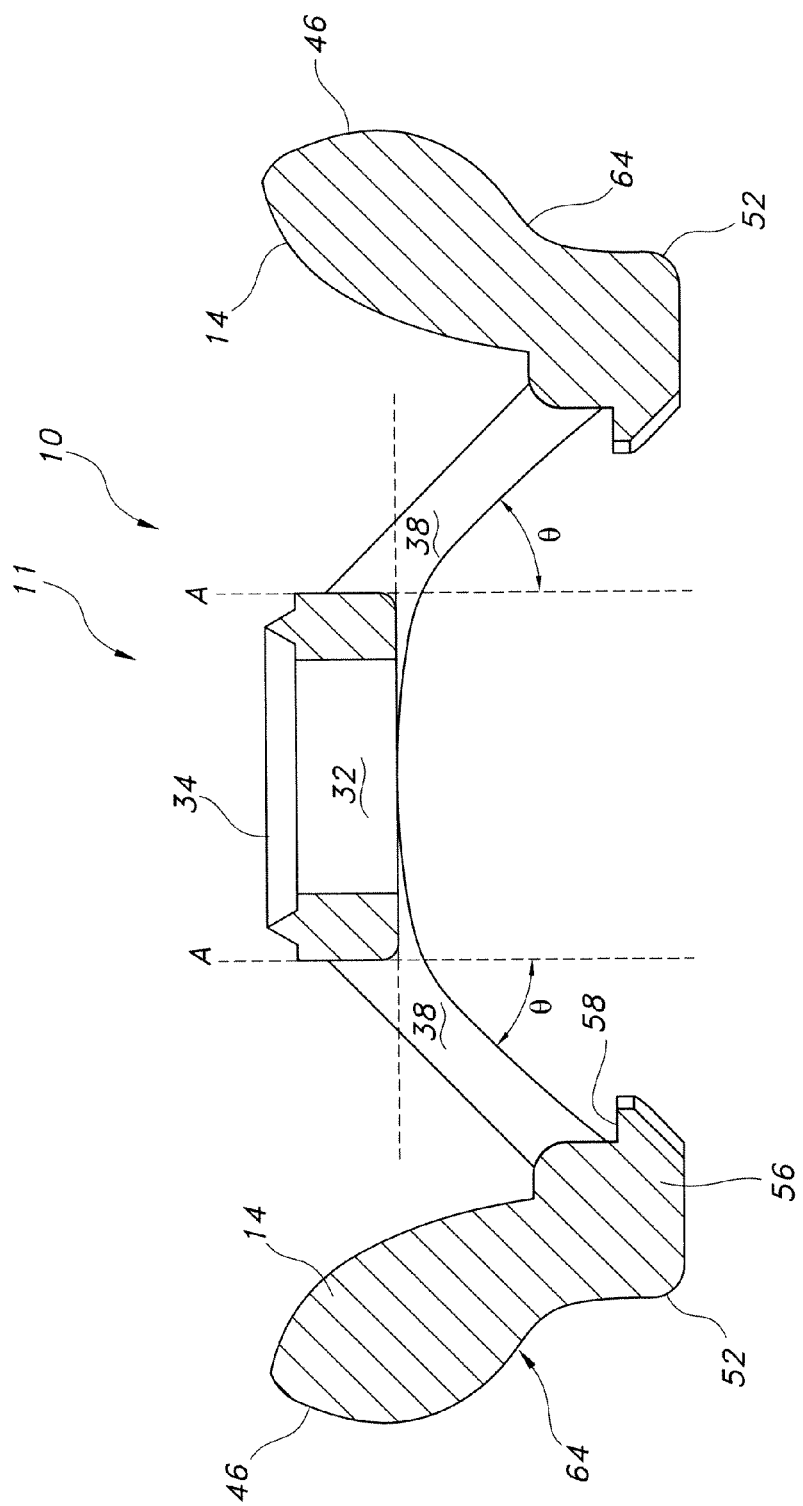
FIG. 10 is a side view illustrating a feature of an example connector highlighting a portion of an exemplary cantilevered spring.

In an aspect of the invention, the upper surface 34 of the central support 32 may be located above the transition 64 between the first portion 46 and second portion 52 of the release button 14. In such a configuration, the arm 38 of a cantilevered spring 36 may define an angle "θ" of between about 35 degrees and about 50 degrees with respect to an axis "A" normal to the central support as generally illustrated in FIG. 10. For example, each arm of a cantilevered spring may define an angle of between about 40 degrees to about 45 degrees with respect to an axis normal to the central support. While the inventors should not be held to any specific theory of operation, the specified angle θ between the arm 38 of the cantilevered spring and the axis "A" normal to the central support is thought to allow sufficient deflection of the arm(s) of the cantilevered spring (when made of suitable plastic or other material including, but not limited to, nylon, polycarbonate, polyurethane or the like) to allow coupling and decoupling of the connector at the predetermined levels of force and without causing premature fatigue of the materials used in the spring.

Figure 11:
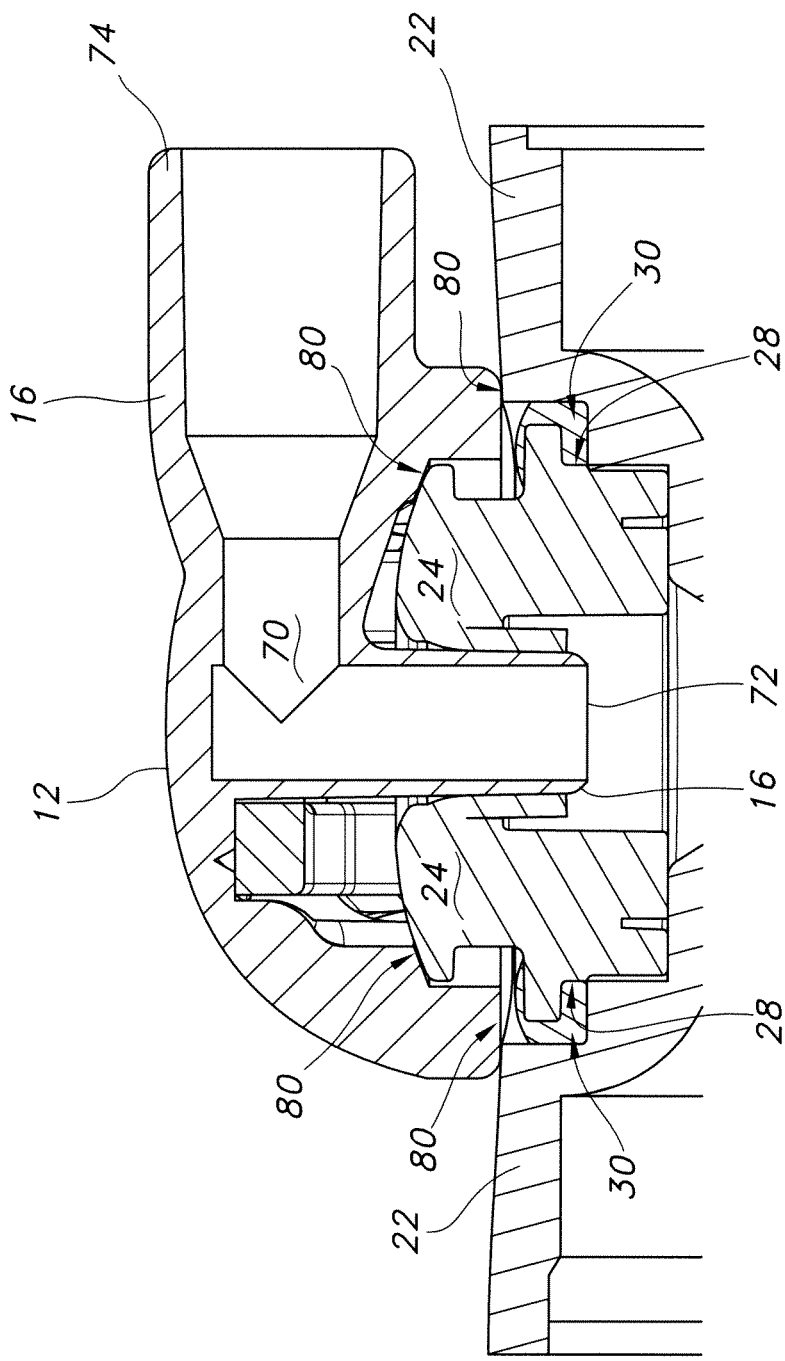
FIG. 11 is a cross-sectional view illustrating a portion of an exemplary connector having a cover or head contacting a circular hub.
Figure 12:
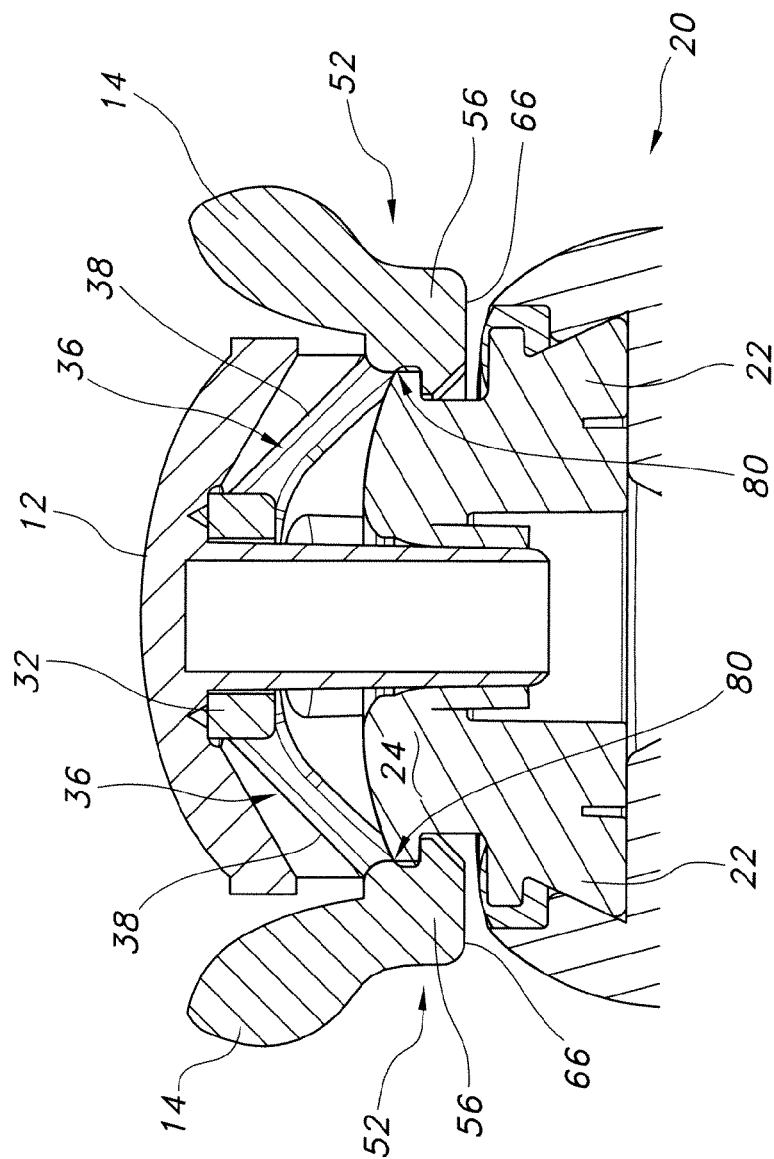
FIG. 12 is a side view illustrating a portion of an exemplary connector and a circular hub on a base of an enteral feeding catheter device.

Referring now to FIG. 11, the connector 10 may further include motion limiters 80 to limit the pitch of the connector. More particularly, FIG. 11 is a cross-sectional view of a portion of an exemplary connector 10 having a cover or head 12 contacting a circular hub 24. A defined fluid pathway 70 may pass through conduit 16 of the connector 10. The motion limiters 80 may be integrated with or joined to part of the cover or head 12 and configured to contact an upper surface of the hub 24 or an upper surface of the base 22 of the enteral feeding catheter device. Alternatively and/or additionally, the motion limiters 80 may constitute a portion of the cantilever springs 36 or catches 56 as generally illustrated in FIG. 12. For example, the arms 38 of the cantilevered springs may be configured to contact a portion of the circular hub 24 to function as motion limiters 80. As yet another example, the bottom face 66 of the second portion 52 of the release button 14 may form a proximal portion of connector 10 (i.e., the portion of the connector that is oriented toward and generally positioned closest to the base 22 of the enteral feeding catheter device 20) and function as a motion limiter 80.

As noted above, the connector may include a cover or head 12. The head 12 may have a clamshell or bowl shape to cover the cantilevered springs 36 and central support 32. The head 12 may be joined to the central support 32 or may be formed as a unitary element with the central support. The head 12 may form a distal portion of the connector i.e., the portion of the connector that is oriented or positioned furthest away from the base 22 of the enteral feeding catheter device 20).

Figure 15:
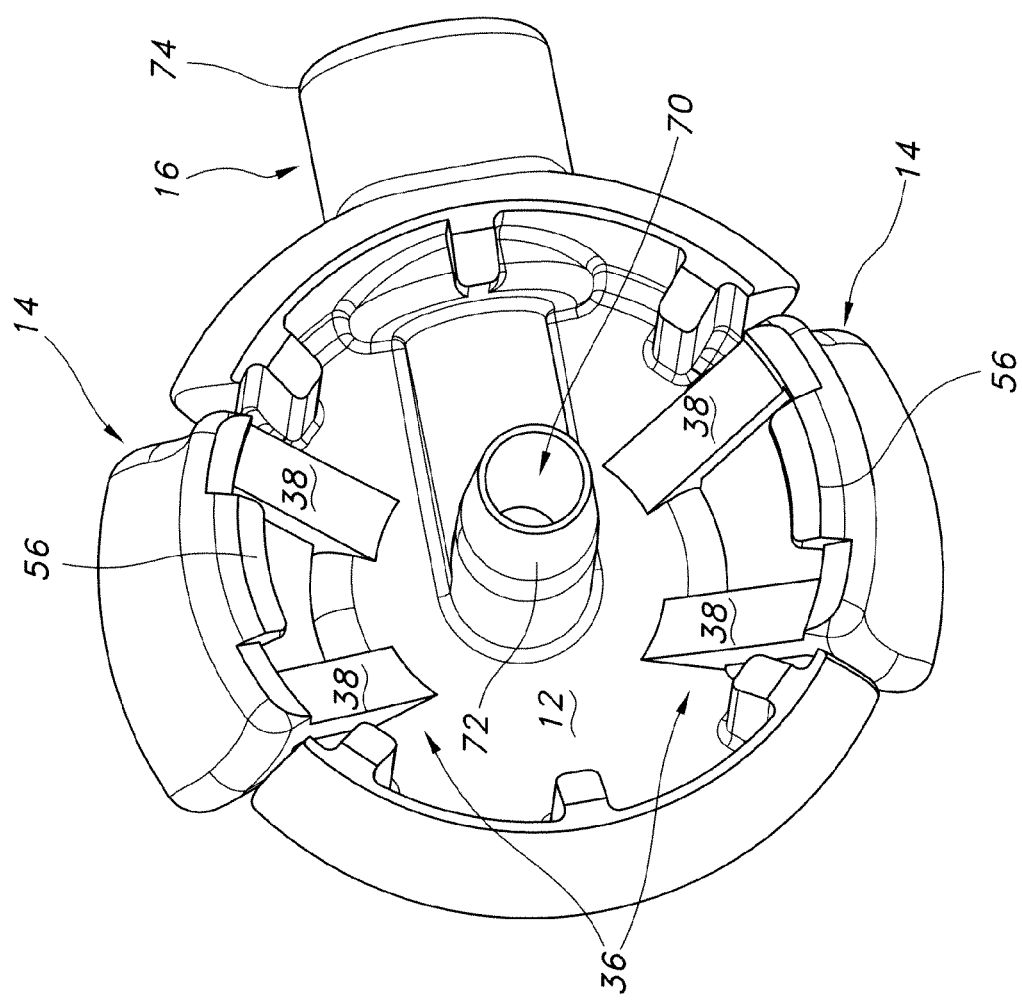
FIG. 15 is a bottom view of an exemplary connector in which the cantilever springs are integrated with or joined to the head or cover.
Figure 16:
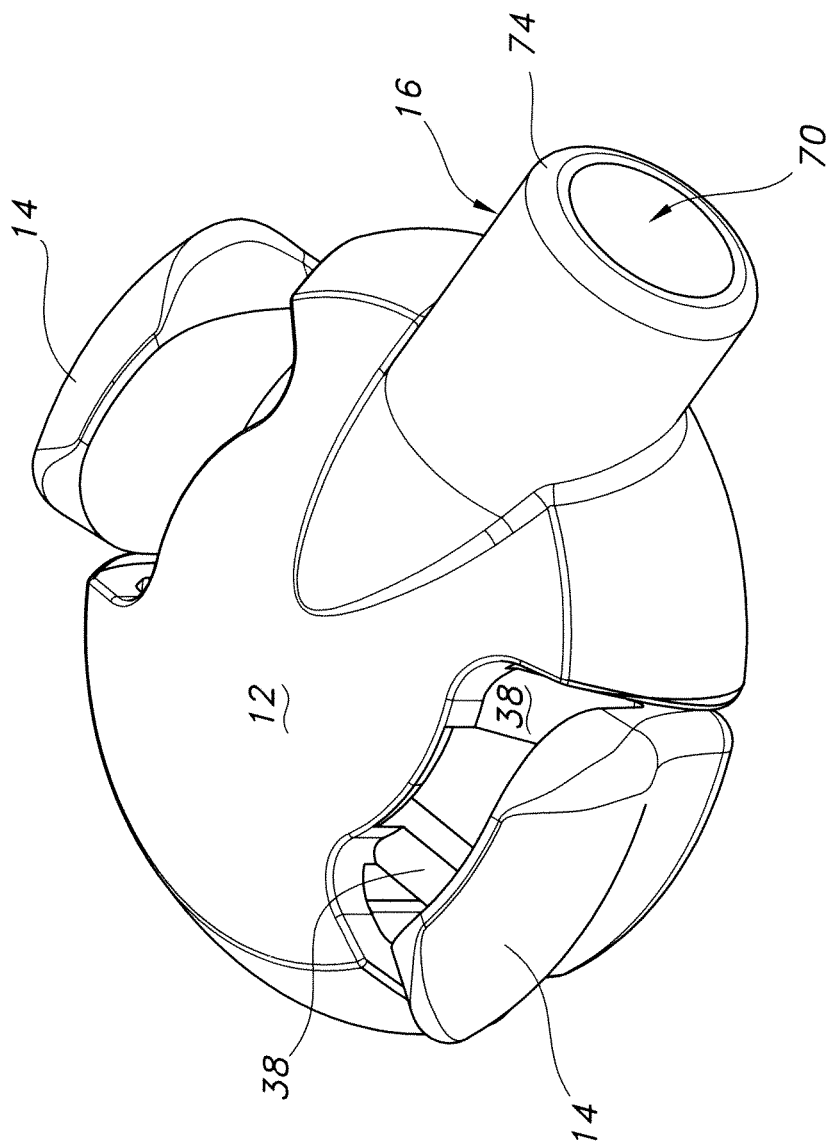
FIG. 16 is a top perspective view showing the exemplary connector of FIG. 15.

According to an aspect of the invention, the cantilever springs 36 may be configured so they are integrated with the head 12 of the connector 10 such that the integrated cantilever springs are able to resiliently bias the release buttons. Referring now to FIG. 15, there is shown a bottom view of an exemplary connector 10 in which the cantilever springs 36 are integrated with or joined to the head or cover 12. That is, the central support 32 illustrated in FIG. 3A may be unitary with the cover 12 such that the arms 38 of the cantilevered springs 36 extend radially outward from a central portion of the cover 12. FIG. 16 is a top perspective view showing the exemplary connector of FIG. 15.

According to the invention, the connector 10 is "rotatably coupled" to the circular hub 24. That is, the connector freely rotates completely about the circular hub when coupled to the base of the enteral feeding catheter device. The connector is configured to freely rotate completely around the hub without passing through a position or location where the connector encounters a feature such as a keyway, a groove, a slot or the like which would allow the connector to be inadvertently disengaged and/or without encountering a feature such as a stop, detent or the like that would inhibit or prevent rotation completely around the hub thereby causing the enteral feeding catheter device to twist. Desirably, the connector is configured to rotate completely around the hub multiple times while providing little or no resistance so that the enteral feeding catheter device does not twist or turn.

The present invention also encompasses an enteral feeding assembly. The enteral feeding assembly is composed of: (i) an enteral feeding catheter device having a base and including a catheter with a lumen positioned through the base, the base having a circular hub having a radius, a top surface, a side surface and a circumferential recess defined in the side surface; and (ii) an extension set connector for rotatably coupling a feeding tube to a base of an enteral feeding catheter device. The extension set connector is the connector as generally described above.

The present invention further encompasses a feeding extension set. The feeding extension set includes a feeding extension tube and a connector for use with an enteral feeding catheter device having a circular hub. The connector has a plurality of resiliently biased release buttons incorporating catches. The connector is configured to rotatably couple to the circular hub by positioning the connector on the hub and depressing the connector until the catches engage a circumferential recess defined in a side surface of the circular hub and the connector is further configured to decouple from the hub by depressing the release buttons to move the respective catches radially outward to disengage from the circumferential recess. The release buttons may be resiliently biased the resilient assembly. The resilient assembly includes at least one resilient element which may be compression springs, extension springs, resilient foams or the like and combinations thereof. If the resilient assembly includes cantilevered springs, each cantilevered spring has at least one arm. Each arm has a first end, a central section, and a second end that is joined to a central support.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

We claim:

1. A connector for coupling a medical fluid supply tube to the head of a catheter device having a circular hub having a generally horizontal top surface that extends radially outward over a generally vertical side surface to define a circumferential recess in the side surface of the circular hub, the connector comprising:
   a resilient assembly including cantilevered springs, wherein each cantilevered spring has at least one arm, each arm having a first end, a central section, and a second end that is joined to a central support; and
   a plurality of release buttons extending from the resilient assembly, each release button having a first portion including a finger contact zone and a second portion including a catch, the catch configured to releasably engage a circumferential recess defined in a side surface of the circular hub,
   wherein the connector is coupled to the circular hub having a generally horizontal top surface that extends radially outward over the generally vertical side surface to define a circumferential recess by positioning the connector on the hub and depressing the connector until the catches engage the circumferential recess such that the connector is free to rotate completely about the circular hub and the connector is decoupled from the hub by pressing the release buttons radially inward to reversibly displace the cantilevered springs thereby moving the respective catches radially outward to disengage them from the circumferential recess.

2. The connector of claim 1, wherein each arm of the cantilevered spring has a length measured from its connection with the release button to its connection with the central support that is from about 0.75 to about 1.25 times the length of the radius of the circular hub.

3. The connector of claim 2, wherein each arm of the cantilevered spring further defines an angle of between about 35 degrees to about 50 degrees with respect to an axis normal to the central support and wherein an upper surface of the central support is located above the transition between the first portion and second portion of the release button.

4. The connector of claim 1, wherein each arm of the cantilevered spring is reversibly displaced when a force of between about 2 Newtons and about 14 Newtons is applied to its respective release button.

5. The connector of claim 1, further comprising motion limiters.

6. The connector of claim 1, wherein each catch has a top surface configured to releasably engage the circumferential recess defined in the side surface of the circular hub and a bottom surface and the bottom surface is beveled.

7. The connector of claim 1, further comprising a conduit defining a fluid pathway through the connector.

8. An enteral feeding assembly comprising:
   an enteral feeding tube device having a base, a tube with at least one lumen positioned through the base, at least one circular hub on the base, the circular hub having a radius, a top surface, a side surface and a circumferential recess defined in the side surface; and
   a feeding extension set including a connector according to claim 1, wherein the connector allows for fluid communication between the feeding extension set and at least one lumen of the enteral feeding tube device.

9. An extension set connector for coupling a feeding extension set to a base of an enteral feeding tube device equipped with a circular hub having a radius, a generally horizontal to surface that extends radially outward over a generally vertical side surface to define a circumferential recess in the side surface, the connector comprising:
   a resilient assembly including cantilevered springs, wherein each cantilevered spring has at least one arm, each arm having a first end, a central section, and a second end that is joined to a central support, and wherein each arm of the cantilevered springs has a length measured from its connection with the release button to its connection with the central support that is from about 0.75 to about 1.25 times the length of the radius of the circular hub;
   release buttons, each release button joined with a respective first end of an arm, each release button having a first portion comprising a finger contact zone on an outer surface, and a second portion comprising a catch on an inner surface, the catch configured to releasably engage the circumferential recess defined in the side surface of the circular hub; and
   a conduit defining a fluid pathway through the connector, the conduit configured to supply a feeding solution to a lumen of the enteral feeding tube device,
   wherein the connector is rotatably coupled to the circular hub having a generally horizontal top surface that extends radially outward over the generally vertical side surface to define a circumferential recess by positioning the connector on the hub and depressing the connector until the catches engage the circumferential recess defined in the side surface of the circular hub, and wherein the connector is decoupled from the hub by pressing the release buttons radially inward to reversibly displace the cantilevered springs thereby moving the respective catches radially outward to disengage from the circumferential recess.

10. The connector of claim 9, wherein each arm of the cantilevered springs further defines an angle of between about 35 degrees to about 50 degrees with respect to an axis normal to the central support and wherein an upper surface of the central support is located above the transition between the first portion and second portion of the release button.

11. The connector of claim 9, wherein each arm of the cantilevered spring is reversibly displaced when a force of between about 2 Newtons and about 14 Newtons is applied to its respective release button.

12. The connector of claim 9, further comprising motion limiters.

13. The connector of claim 9, wherein the cantilevered springs comprise a pair of cantilevered springs in opposed relationship and the release buttons comprise a pair of release buttons.

14. The connector of claim 9, further comprising a head joined to the central support.

15. The connector of claim 9, wherein the conduit further comprises a nozzle that is configured to engage an orifice defined in the hub to supply a feeding solution to a lumen of an enteral feeding tube device.

16. The connector of claim 9, wherein each catch has a top surface configured to releasably engage the circumferential recess defined in the side surface of the circular hub and a bottom surface and the bottom surface is beveled.

17. A feeding extension set, comprising:
   an enteral feeding extension tube; and
   a connector in fluid communication with the enteral feeding extension tube, the connector configured for rotatably coupling the enteral feeding extension tube to an enteral feeding tube device having a circular hub including a generally horizontal top surface that extends radially outward over a generally vertical side surface to define a circumferential recess in the side surface of the circular hub, the connector comprising:

a resilient assembly including cantilevered springs, wherein each cantilevered spring includes at least one arm having a first end, a central section, and a second end that is joined to a central support; and a plurality of release buttons extending from the resilient assembly, each release button having a first portion including a finger contact zone and a second portion including a catch, the catch configured to releasably engage a circumferential recess defined in a side surface of the circular hub, wherein the connector is coupled to the circular hub having a generally horizontal top surface that extends radially outward over the generally vertical side surface to define a circumferential recess by positioning the connector on the hub and depressing the connector until the catches engage the circumferential recess such that the connector is free to rotate completely about the circular hub and the connector is decoupled from the hub by pressing the release buttons radially inward to reversibly displace the cantilevered springs thereby moving the respective catches radially outward to disengage them from the circumferential recess.

* * * * *